United States Patent [19]

Ziman

[11] 4,009,179
[45] Feb. 22, 1977

[54] DI- AND TRI-SUBSTITUTED OXAZOLIDIN-2-ONE OXIMES

[75] Inventor: Stephen David Ziman, Richmond, Calif.

[73] Assignee: E. I. Du Pont de Nemours and Company, Wilmington, Del.

[22] Filed: Oct. 15, 1975

[21] Appl. No.: 622,673

[52] U.S. Cl. .................... 260/307 FA; 260/30.4 R; 260/296 M; 260/345.9; 424/263; 424/272

[51] Int. Cl.² ....................................... C07D 263/28

[58] Field of Search ................. 260/307 FA, 296 M

[56] References Cited

UNITED STATES PATENTS 3,875,232  4/1975  Magee ............................... 260/566

Primary Examiner—Raymond V. Rush
Attorney, Agent, or Firm—Anthony P. Mentis

[57] ABSTRACT

Certain di- and tri- substituted oxazolidin-2-one oximes have antidepressant activity in warm blooded animals. Exemplary is 4-methyl-5-phenyl-2-oxazolidinone oxime.

8 Claims, No Drawings

DI- AND TRI-SUBSTITUTED OXAZOLIDIN-2-ONE OXIMES

BACKGROUND OF THE INVENTION

1. Field of the Invention

This invention relates to substituted oxazolidin-2-one oximes which are useful as plasticizers for polyvinyl chloride. Some have antidepressant properties in warm blooded animals.

2. Prior Art 2-oxazolidinone has been described in the literature (Chem Abs. 69, 97124d) and one substitution product

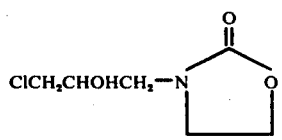

has been reported (Chem. Abs. 72, 31662h). No oximes or other substitution products have been reported or methods suggested whereby oximes or 2-oxazolidinones having substituents on nuclear carbon can be obtained.

SUMMARY OF THE INVENTION

This invention is an oxazolidin-2-one oxime of the formula

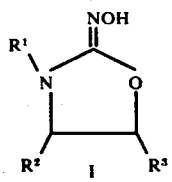

wherein $R^1$ and $R^2$ individually are H, alkyl of 1–3 carbons alkenyl of 2–3 carbons, phenyl or benzyl; and $R^3$ is H, alkyl of 1–3 carbons, benzyl, pyridyl, indolyl having up to one methyl or phenyl substituent, or phenyl or naphthyl having up to one nitro or methylenedioxy substituent or up to two substituents of halogen, alkyl of 1—3 carbons or alkoxy of 1-3 carbons.

Preferred for their biological activity, e.g., antidepressant properties, are compounds where $R^1$ is H or alkyl of 1-3 carbons;

$R^2$ is H or methyl; and $R^3$ is benzyl or phenyl containing up to two substituents of halogen, alkyl of 1-3 carbons or alkoxy of 1-3 carbons.

The compounds can be prepared by the general reaction

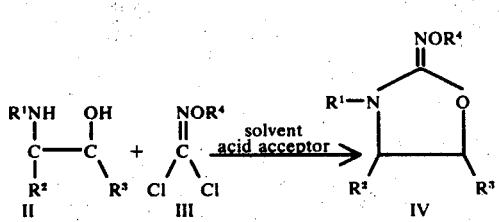

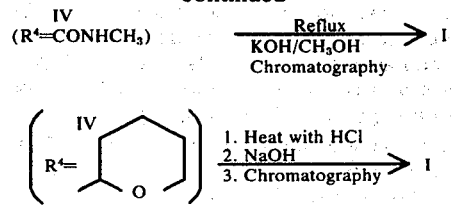

The reaction involves heating an alkanolamine II (in which $R^1$, $R^2$, and $R^3$ have the values previously given) with a phosgene oxime reactant III in the presence of an inert solvent and an acid acceptor such as trimethylamine or triethylamine to give the oxime ether IV. This is then hydrolyzed to give the product I.

In place of the alkanolamine II, its alkali metal alkoxide can be used. The latter is prepared by reaction of II with molar amounts of an alkali metal alkyl or hydride.

The reactant III is phosgene oxime O-N-methylcarbamate when $R^4$ is $=CONHCH_3$ and is phosgene oxime O-tetrahydropyran when $R^4$ is

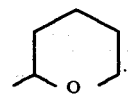

The inert solvent is exemplified by dimethylformamide, benzene, toluene, tetrahydrofuran, acetonitrile, chloroform, dioxane, and the like.

The temperature of the reaction process is 60°–100° C and the time is 2–12 hours.

O-Tetrahydropyranyl phosgene oxime is prepared as follows:

Dihydropyran (2.52 g, 0.03 mol) and phosgene oxime (3.6 g, 0.03 mol) are dissolved in 100 ml tetrahydrofuran (THF). To this is added 2 drops of phosphorous oxychloride and mixture refluxed for 12 hr. The solvent is then evaporated and resultant liquid is distilled, giving a colorless liquid, bp 97–107/20 mm Hg. Redistillation is done at a lower pressure; bp 62–63/0.7 mm, yield 3.4 g (58%).

Nmr: ($CDCl_3$)1.32–2.10 (m, 6H), 3.40–4.20 (m, 2H), 5.35 (bs, 1H).

Mass spectrum; M = 197. Other peaks are: 139, 113, 96, 85.

SPECIFIC EMBODIMENTS OF THE INVENTION

The following are illustrative examples in which all parts are by weight and all temperatures are Centigrade unless otherwise stated.

EXAMPLE 1

4-Methyl-5-phenyl-2-oxazolidinone oxime

All equipment was dried before use. Norephedrine ($C_6H_5CHOHCH(CH_3)NH_2$) (3.0 gm, 0.02 M) was dissolved in 100 ml dry tetrahydydrofuran (THF) and cooled to 0°. One equivalent (12.8 ml of 1.54 M) n-butylithium was added via syringe and the solution stirred for 1 hr. Phosgene oxime O-tetrahydropyranyl ether (3.94 gm, 0.02 mol) in 10 ml dry THF was added dropwise over 20 minutes. This was stirred for 1 hr, then 2.0 gm (0.02 mol) triethylamine was added to the solution and it was refluxed for 4 hr. The THF was evaporated and the crude material was hydrolyzed with 50 ml of 1 N HCl for 1 hr. on a steam bath. The aqueous layer was extracted twice with 100 ml CHCl$_3$. The aqueous layer was then made basic (pH 10), re-extracted with 2 × 100 ml CHCl$_3$ and 1.20 gm of crude product was recovered. From this 0.28gm of a white solid, m.p. 145°–148° was isolated.

The physical data for this compound, and others, are set out in Table I. The compounds of Examples 1–9 and 12–14 were prepared by the above general procedure using phosgene oxime O-tetrahydropyranyl ether. In place of n-butyllithium, Examples 2–6 and 8 used NaH while Examples 7, 9–11 and 14 did not use an alkali metal salt but a further equivalent of tertiary amine. The compounds of Example 10 and 11 were prepared using phosgene oxime-O-(N-methyl)carbamate. This method is illustrated by the following preparation of the compound of Example 10.

p-Fluoroephedrine (2.80 gm, 0.015 mol) was dissolved in 100 ml dry dioxane along with triethylamine (1.6 gm, 0.015 mol). This was heated to reflux and phosgene oxime-O-(N-methyl)-carbamate (2.61 gm, 0.015 mol) in 25 ml dioxane was added dropwise over 0.5 hr. After 1 hr. at reflux, a second equivalent of triethylamine (1.6 gm, 0.015 mol) was added and the solution refluxed overnight. The solvent was then evaporated and the residue dissolved in methanol (100 ml). Potassium hydroxide (8.4 gm, .15 mol) was added and the solution refluxed for 8 hr. The methanolic solution was then poured into 200 ml water, extracted with 2 × 100 ml chloroform; the organic layer dried (MgSO$_4$) and solvent evaporated. The residue was chromatographed on a silicar CC-7 column, eluting with chloroform and increasing percentages of ethanol. There was obtained 1.0 g (30% yield) of a yellow oil. Spectral data confirm its structure as shown in Table I.

TABLE I

| Example No. | Compound | NMR (δ) (in CDCl$_3$) | Analysis (Mass Spectrum) | Mp ° C |
|---|---|---|---|---|
| 1 | (structure with NOH, HN, CH$_3$, C$_6$H$_5$) | 0.76 (d, J=6.5Hz, 3H) 4.15 (t, J=7Hz, 1H), 5.58 (d, J=7Hz, 1H), 7.38 (s, 5H). | Calcd. for C$_{10}$H$_{12}$N$_2$O$_2$: 192.0898 Found: 192.0883 | 145–148 |
| 2 | (structure with NOH, CH$_3$, methylenedioxyphenyl) | 2.79 (s, 3H), 2.90–3.15 (m, 1H) 3.55 (t, J-8Hz,- 1H), 4.30 (m, 1H), 5.95 (s, 2H) 6.66–7.00 (m, 3H) | Calcd. for C$_{11}$H$_{12}$N$_2$O, 236.0796 Found: 236.0779 | 186–190 |
| 3 | (structure with CH$_3$, CH$_3$, CH, NOH, methylenedioxyphenyl) | 1.12 and 1.18 (pr of d, J=7Hz, 6H), 2.60–4.50 (m, 4H), 5.95 (s, 2H) 6.75–7.0 (m, 3H). | Calcd. for C$_{13}$H$_{11}$N$_2$O$_4$, 264.1109 Found: 264.1059 | 154–156 |
| 4 | (structure with N—OH, C$_2$H$_5$, methylenedioxyphenyl) | 1.13 (t, J=7Hz, 3H), 2.82– 3.78 (m, 4H), 4.32–4.70 (m, 1H), 5.92 (s, 2H), 6.78–7.00 (m, 3H). | Calcd. for C$_{12}$H$_{14}$N$_2$O$_4$, 250.0953 250.0976 | 116–121 |
| 5 | (structure with NOH, CH$_3$, p-methoxyphenyl) | 2.83 (s, 3H), 2.95–3.85 (m, 2H), 3.77 (s, 3H), 4.34–4.70 (m, 1H) 7.10 (A$_2$B$_2$, 4H). | Calcd. for C$_{11}$H$_{14}$N$_2$O$_3$; 222.1004 Found: 222.1026 | Oil |

TABLE I-continued

| Example No. | Compound | NMR (δ) (in CDCl$_3$) | Analysis (Mass Spectrum) | Mp °C |
|---|---|---|---|---|
| 6 | 3-methyl-5-(3,4-dimethoxyphenyl)-2-hydroxyimino-oxazolidine | 2.83 (s, 3H), 2.95–3.85 (m, 2H) 3.85 (s, 3H), 3.89 (s, 3H), 4.33–4.70 (m, 1H) 6.80–7.10 (m, 2H). | | Oil |
| 7 | 3,4-dimethyl-5-phenyl-2-hydroxyimino-oxazolidine | 0.75 (d, J=6Hz, 3H), 2.68 (s, 3H), 3.81 (5, J-7Hz, 1H), 5.55 (d, J=7Hz, 1H), 7.29 (s, 5H) | Calcd. for C$_{11}$H$_{14}$N$_2$O$_2$: 206.1054 Found: 206.1048 | Oil |
| 8 | 3-isopropyl-5-phenyl-2-hydroxyimino-oxazolidine | 1.13 and 1.19 (pair d, J= 6.5Hz, 6H), 3.27 (t, J=7Hz, 1H), 3.50–4.15 (m, 2H), 5.50 (t, J=7Hz,1H) 7.38 (s, 5H) | Calcd. for C$_{12}$H$_{16}$N$_2$O$_2$: 220.1211 Found: 220.1204 | 106–109 |
| 9 | 3-methyl-5-benzyl-2-hydroxyimino-oxazolidine | 2.67 (s, 3H), 2.75–3.50 (m, 4H), 4.70 (d of t, 1H) 7.25 (s, 5H) | Calcd. for C$_{11}$H$_{14}$N$_2$O$_2$: 206.1054 Found: 206.1054 | Oil |
| 10 | 3,4-dimethyl-5-(4-fluorophenyl)-2-hydroxyimino-oxazolidine | 0.75 (d, J=6,5Hz, 3H), 2.66 (s, 3H) 3.80 (t, J=7Hz, 1H), 5.52 (d, J=7Hz, 1H) 6.85–7.45 (m, 4H), | Calcd. for C$_{11}$H$_{13}$FN$_2$O$_2$: 224.0960 Found: 224.0954 | Oil |
| 11 | 3,4-dimethyl-5-(4-chlorophenyl)-2-hydroxyimino-oxazolidine | Mixture of four isomers | Calcd. for C$_{11}$H$_{13}$ClN$_2$O$_2$: 240.0665 Found: 240.0691 | Oil |
| 12 | 3,4-dimethyl-5-(1-methylindol-3-yl)-2-hydroxyimino-oxazolidine | 1.30 (d, J=7Hz, 3H) 2.82 (s, 3H), 3.10–3.68 (m, 1H), 3.80 (s, 3H), 4.28 (d, 1H), 7.08–7.45 (m, 4H), 7.68–7.90 (m, 1H). | Calcd. for C$_{14}$H$_{17}$N$_3$O$_2$: 259.1320 Found: 259.1307 | Oil |

TABLE I-continued

| Example No. | Compound | NMR (δ) (in CDCl₃) | Analysis (Mass Spectrum) | Mp °C |
|---|---|---|---|---|
| 13 | 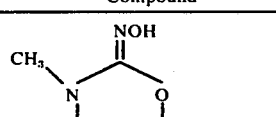 | 1.33 (d, J=7Hz, 3H) 2.83 (s, 3H), 4.25–4.50 (m, 1H), 7.25 (s, 5H), 7.30–7.60 (m, 4H), 7.68–7.85 (m, H). | Calcd. for $C_{19}H_{19}N_3O_2$: 321 Found: 321 with some at 247 and 220.193 | Oil |
| 14 | 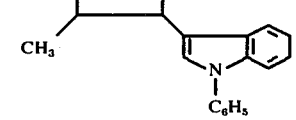 | 1.25 (d, J=7Hz, 3H), 2.85 (s, 3H), 3.30–3.65 (m, 1H), 4.12 (d, J=9Hz,1H), 6.85–8.00 (m, 4H), 8.20–8.50 (m, 1H). | Calcd. for $C_{13}H_{15}N_3O_2$: 245.1163 Found: 245.1149 | 194–6 (dec) |

The ethanolamine precursors used in the syntheses of some of the oxazolinone oximes of Table I are based on (a) known naturally occurring biologically active ethanol amines, (b) reaction of a substituted amine with an aromatic epoxide, or (c) reaction of a substituted benzaldehyde with lithium acetylide to form the yne-ol, followed by hydration of the triple bond with mercuric oxide/methanol/water and then reductive amination with the desired amine and sodium borohydride/methanol. The following Table II gives new substituted ethanolmines used in the preceding examples. The last three in the table were prepared by method (c) and the others by method (b).

Substituted ethanolamines of the structure $R^3CHOHCR^2HNHR^1$ useful in the preparation of the substituted oxazolidin-2-one oximes include those where one of the $R^1$ groups is aromatic and preferably contains a benzenoid group. Those where $R^3$ is an aromatic group are particularly useful and can be prepared as described subsequently. Where either $R^1$ or $R^2$ are aromatic, e.g., $CH_3CHOHCH(C_6H_5)NHCH_3$, $CH_3CHOHCH_2NHC_6H_5$ and related compounds are available as described in chemical literature.

New compounds obtainable by the general processes described include the following:

TABLE II

| INTERMEDIATE FOR EXAMPLE | ETHANOL AMINES | NMR (δ) |
|---|---|---|
| 2 | (structure with benzodioxole, OH, NHCH₃) | (CDCl₃) H₃O⁺) 2.98 (t, J = 1Hz,3H) 3.22–3.60 (m, 2H), 5.16 (t, J = 7Hz, 1H) 6.00 (s, 2H), 6.70–7.05 (m, 3H) |
| 3 | (structure with benzodioxole, OH, NH-C₃H₇(i)) | (CDCl₃) 1.08 (d, J = 7Hz, 6H), 2.60–2.85 (m, 2H), 3.37 (s) and 3.35–3.90 (m) 3H, 4.50–4.80 (m, 1H), 5.90 (s, 2H) 6.73–6.95 (m, 3H) |
| 4 | (structure with benzodioxole, OH, NH–C₂H₅) | (CDCl₃, CF₃CO₂H) 2.95 (t, J = 7Hz, 3H) 3.85 (s, 3H), 7.11 (A₂B₂, 4H). |
| 5 | (structure with CH₃O-phenyl, OH, NHCH₃) | (CDCl₃, CF₃CO₂H) 2.95 (t, J = 7Hz, 3H) 3.85 (s, 3H) 7.11 (A₂B₂, 4H). |
| 6 | (structure with CH₃O, CH₃O-phenyl, OH, NHCH₃) | (CDCl₃) 3.42 (bs, 3H), 3.85 (s, 6H), 3.50–3.90 (m, 2H), 4.55–4.90 (m, 1H) |
| 10 | (structure with F-phenyl, OH, NH–CH₃, CH₃) | Nmr is mixture of erythio and threo compounds |
| 11 | (structure with Cl-phenyl, OH, NHCH₃, CH₃) | Nmr is a mixture of threo and erythreo compounds |

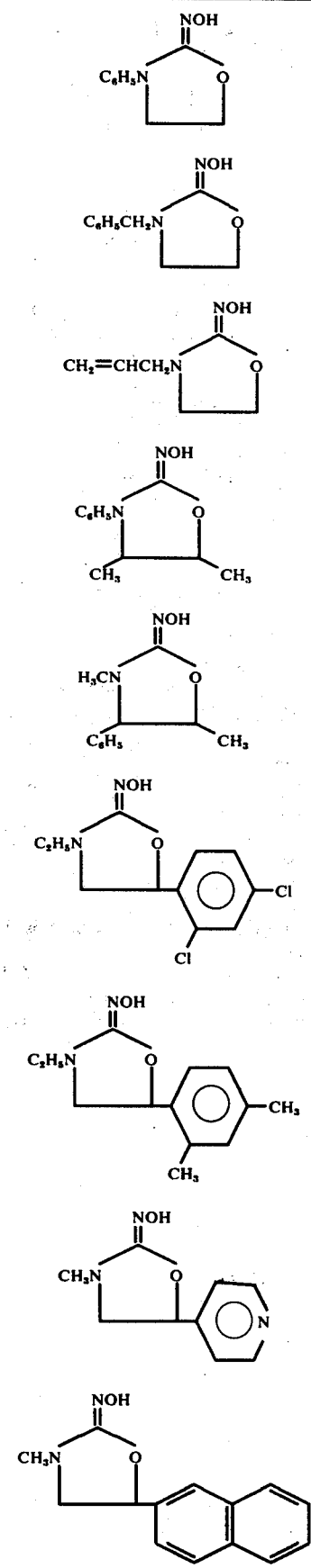

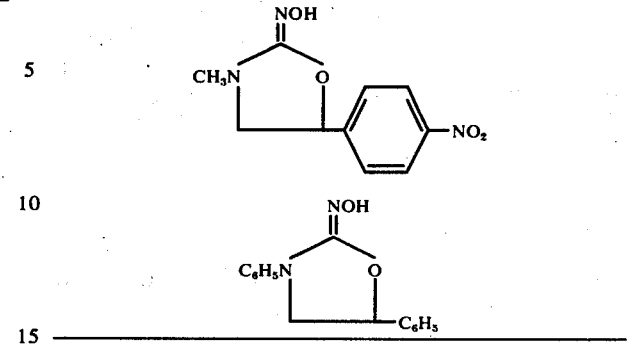

EXAMPLE A

To a 2 ml sample of Geon 128 PVC (10% solution in THF), 100 mg of 3-isopropyl-5-phenyl-2-oxazolidinone oxime was added and mixed until the solution was homogeneous. The sample was then spread on a petri dish, covered, and allowed to set for 24 hr. A standard 2 ml sample without any oxazolidinone oxime was run under the same conditions. Removal of the films showed that the oxazolidinone oxime acted as a plasticizer. The film was very flexible and bent and folded easily, unlike the standard which is much less flexible. The thickness of the test film was between $4.5-5.0 \times 10^{-4}$ inch and that of the standard was $2.0-2.8 \times 10^{-4}$ inches.

The compounds of this invention which are useful as antidepressants can be employed in pharmaceutical compositions composed of the active ingredient, i.e., the compound(s) of the invention, in combination with non-toxic pharmaceutical carriers and additives. In any formulation of the antidepressant agent, the active ingredient will oridinarily be present in an amount from about 0.5% to 95% based on total weight of the composition.

Formulations include injectables and oral dosage forms such as tablets, hard and soft gelatin capsules, suspensions, syrups, elixers and the like. Additives that can be employed in such formulations include solvents and diluents, lubricants, binding agents, disintegrants, preservatives, colorants, flavors and other additives.

The compounds of this invention can be administered in a pharmaceutical carrier as treatment for psychiatric depressions of the reactive and endogenous types by any means that effects contact of the active ingredient compound with the site of action in the body of a warm blooded animal. For example, administration can be parenterally, i.e., subcutaneously, intravenously, intramuscularly or intraperitoneally. Alternatively or concurrently, administration can be by the oral route.

The dosage administered will be dependent upon the age, health and weight of the recipent, the type and severity of depression, kind of concurrent treatment, if any, frequency of treatment and the nature of the effect desired. Generally, a daily dosage of active ingredient compound will be from about 0.01 to 50 mg/kg of body weight. Ordinarily, from 0.05 to 40 and preferably 0.1 to 10 mg/kg per day in one or more applications per day is effective to obtain desired results.

The antidepressant activity of the compounds is evidenced by tests conducted in female white mice in which prevention of tetrabenazine-induced sedation and depression was demonstrated. This mouse test is predictive of human antidepressant response (Everett, G. M., "The Dopa Response Potentiation Test and Its Use in Screening for Antidepressant Drugs", p.p. 164-167 in "Antidepressant Drugs", Proceedings of the First International Symposium, S. Garattini and M. N. G. Dukes, cds., 1967).

EXAMPLE B

Groups of 10 Carworth CF₁S female mice, 18-21 g. each, were fasted 1.5 hours and were intubated with selected oxazoline oximes as antagonist to tetrabenazine at oral doses of 5, 25 and 125 mg/kg in 0.20 ml of 1% methyl cellulose (Methocel). Thirty minutes later the mice were challenged with tetrabenazine, 32 mg/kg intraperitoneally (dissolved in 0.20 ml of 0.05M KCl at pH 2.0). One hour after the oxazolidinone oxime compound (30 minutes after tetrabenazine) the mice were examined for signs of exploratory activity and ptosis (eyelid closure). Normal exploratory activity (relief from sedation) was recorded when a mouse lifted by the tail from a group of 10 in a testing box and placed on a stainless steel testing box lid (12.5 inch, × 8 inch, with 0.33 mesh) either turned its head horizontally 30° or moved to the edge of the screen within 10 seconds after being placed on the screen. Relief from ptosis was recorded when exactly 2 seconds after placing the mouse facing the observer, lid closure was less than 50% in both eyes.

With relief of ptosis as the criterion, oxazolidinone oximes prevent tetrabenazine-induced sedation in mice. The ptosis and exploratory loss ED₅₀, i.e., the dose which blocked ptosis and exploratory loss in 50% of the mice, is given in the following table:

| Compound of Example No. | Ptosis | Expl. Loss |
|---|---|---|
| 1 | 1.2 | 2.4 |
| 7 | 2.3 | 4.7 |
| 8 | 8 | 17.4 |
| 9 | 13 | 32 |
| 10 | 2 | 3 |
| 11 | 33 | 81 |

I claim:

1. A compound of the formula

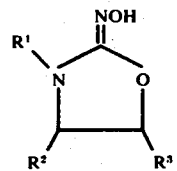

wherein
R¹ and R² individually are H, alkyl of 1-3 carbons, alkenyl of 2-3 carbons, phenyl or benzyl; and
R³ is H, alkyl of 1-3 carbons, benzyl, pyridyl, indolyl having up to one methyl or phenyl substituent, or phenyl or naphthyl having up to one nitro or methylenedioxy substituent or up to two substituents of halogen, alkyl of 1-3 carbons or alkoxy of 1-3 carbons.

2. A compound of the formula

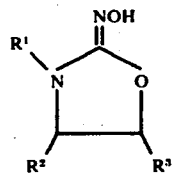

wherein
R¹ is hydrogen or alkyl of 1-3 carbons;
R² is hydrogen or methyl; and
R³ is benzyl or phenyl containing up to two substituents of halogen, alkyl of 1-3 carbons or alkoxy of 1-3 carbons.

3. The compound of claim 2 which is 4-methyl-5-phenyl-2-oxazolidinone oxime.

4. The compound of claim 2 which is 3,4-dimethyl-5-phenyl-2-oxazolidinone oxime.

5. The compound of claim 2 which is 3-isopropyl-5-phenyl-2-oxazolidinone oxime.

6. The compound of claim 2 which is 3-methyl-5-benzyl-2-oxazolidinone oxime.

7. The compound of claim 2 which is 3,4-dimethyl-5-p-fluorophenyl-2-oxazolidinone oxime.

8. The compound of claim 2 which is 3,4-dimethyl-5-p-chlorophenyl-2-oxazolidinone oxime.

* * * * *